United States Patent [19]

Herman

[11] Patent Number: 5,364,879
[45] Date of Patent: Nov. 15, 1994

[54] MEDICAL USES OF TRIOXOLANE AND DIPEROXIDE COMPOUNDS

[75] Inventor: Stephen Herman, Jupiter Island, Fla.

[73] Assignee: Cliveden Ltd., Nassau, Bahamas

[21] Appl. No.: 195,983

[22] Filed: Feb. 14, 1994

Related U.S. Application Data

[60] Continuation of Ser. No. 996,503, Dec. 23, 1992, abandoned, which is a continuation of Ser. No. 813,962, Dec. 24, 1991, abandoned, which is a continuation-in-part of Ser. No. 456,216, Dec. 20, 1989, abandoned, which is a division of Ser. No. 211,378, Jun. 24, 1988, abandoned.

[51] Int. Cl.$^5$ .................... A01N 43/26; A01N 37/02; A01N 31/00
[52] U.S. Cl. .................... 514/452; 514/463; 514/714; 514/724; 514/762; 514/869; 514/901; 514/966; 514/967; 424/49; 424/DIG. 14; 424/DIG. 15; 604/347; 252/174
[58] Field of Search .............. 514/452, 463, 714, 724, 514/762, 869, 901, 966, 967; 424/49, DIG. 14, DIG. 15; 604/347; 252/174

[56] References Cited

U.S. PATENT DOCUMENTS

| 925,590 | 6/1909 | Neel | 549/431 |
|---|---|---|---|
| 1,210,949 | 1/1917 | Knox | 549/431 |
| 1,910,564 | 5/1933 | Rankin | 549/431 |
| 2,083,572 | 6/1937 | McKee | 424/613 |
| 2,243,053 | 5/1941 | Ramage | 568/959 |
| 2,356,062 | 8/1944 | Johnson | 260/410.7 |
| 2,750,411 | 6/1956 | Fisher et al. | 562/505 |
| 3,360,472 | 12/1967 | Renold | 252/186.26 |
| 3,504,038 | 3/1970 | Beal | 568/469 |
| 4,163,800 | 8/1979 | Wickett et al. | 424/326 |
| 4,451,480 | 5/1984 | DeVillez | 514/859 |
| 4,591,602 | 5/1986 | DeVillez | 514/463 |
| 4,632,980 | 12/1986 | Zee et al. | 530/380 |
| 4,816,478 | 3/1989 | Thornfeldt | 514/450 |
| 5,093,326 | 3/1992 | Herman | 514/172 |
| 5,270,344 | 12/1993 | Herman | 514/725 |

FOREIGN PATENT DOCUMENTS

| 27371 | of 1912 | United Kingdom . |
| 787748 | 12/1957 | United Kingdom . |
| 8912626 | 12/1989 | WIPO . |

OTHER PUBLICATIONS

P. Bailey et al., "Complexes and Radicals Produced during Oxonation of Olefins." *Ozone Reactions with Organic Compounds*, Advances in Chemistry, Series 112, pp. 1–8 (1972).

R. Murray et al., "Ozonolysis: Formation of Cross Diperoxides," *Ozone Reactions with Organic Compounds*, Advances in Chemistry, Series 112, pp. 9–21 (1972).

Criegee and Korber, "Fragmentation of Ozonides by Solvents," *Ozone Reactions with Organic Compounds*, Advances in Chemistry, Series 112, pp. 23–24 (1972).

Tomas Hudlicky, *McGraw-Hill Encyclopedia of Chemistry*, Fifth Edition, 1982, pp. 1035, pp. 1035–1038.

*Primary Examiner*—Nathan M. Nutter
*Attorney, Agent, or Firm*—Lalos & Keegan

[57] ABSTRACT

The present invention provides a method of medical treatment for a medical condition in a mammal. In this method, a pharmacologically effective amount for treatment of the condition of a trioxolane or a diperoxide of a non-terpene unsaturated hydrocarbon is applied to the mammal. The invention also provides methods of modulating the immune system in a mammal, of treating inflammation of a tissue in a mammal, and of treating bacterial, fungal, protozoal and viral infections in a mammal.

11 Claims, No Drawings

MEDICAL USES OF TRIOXOLANE AND DIPEROXIDE COMPOUNDS

RELATED APPLICATIONS

This application is a continuation of application Ser. No. 07/813,962 filed Dec. 24, 1991, now abandoned which is a continuation-in-part of U.S. patent application Ser. No. 456,216, filed Dec. 20, 1989 and now abandoned, which is a divisional of U.S. patent application Ser. No. 211,378, filed Jun. 24, 1988 and now abandoned. The disclosures of all of these previous applications are hereby incorporated herein in their entirety by reference thereto.

BACKGROUND OF THE INVENTION

This invention relates to trioxolane and diperoxide compounds. More particularly, it relates to formation of these compounds from unsaturated hydrocarbons and pharmaceutical preparations including these compounds for treating or preventing medical conditions. It also relates to methods of treating or preventing medical conditions using the trioxolane and diperoxide compounds.

A trioxolane compound is herein defined as a compound of the general structure:

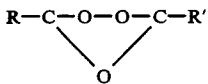

wherein R and R' represent the same or different organic moieties. The indicated carbons may also have additional organic moiety branches.

A diperoxide compound is herein defined as a compound of the general structure:

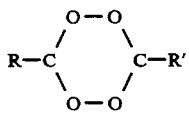

wherein R and R' represent the same or different organic moieties. The indicated carbons may also have additional organic moiety branches.

Procedures for ozonating oil-soluble compounds are known in the art, being disclosed, for example, in U.S. Pat. No. 925,590 to Neel, U.S. Pat. No. 2,083,572 to McKee, and U.S. Pat. No. 4,451,480 to De Villez. However, not all ozonation reactions result in the production of trioxolane and diperoxide compounds. The production of such compounds from unsaturated hydrocarbons is disclosed in Murray et al., "Ozonolysis: Formation of Cross Diperoxides" and Criegee et al, "Fragmentation of Ozonides by Solvents," both in *Ozone Reactions with Organic Compounds*, Advances in Chemistry Series 112, American Chemical Society, Washington, D.C. (1972). The disclosures of these two references are incorporated herein in their entirety by reference thereto.

Ozonation of olefins is generally recognized in terms of a mechanism postulated by Criegee, supra. This mechanism provides that ozone reacts with an unsaturated bond to form an initial, unstable primary ozonide (R—C—$O_3$—C—R'). This primary ozonide readily decomposes to form a zwitterion and a carbonyl fragment. These fragments can then combine to give a trioxolane compound. Under other conditions, the zwitterion may dimerize to form a riperoxide derivative.

The prior art discloses that some particular types of ozonated chemical compositions have certain pharmacological activities. However, as far as Applicants can ascertain, none of these compositions appear to have been prepared in a manner likely to result in the formation of substantial quantities of diperoxide or trioxolane compounds.

In U.S. Pat. No. 925,590, Neel discloses the use of ozonated hydrocarbons for inhalation therapy, because it was believed to have a therapeutic effect for consumption and asthma. Even had the ozonation system of Neel resulted in the formation of substantial quantities of diperoxide or trioxolane compounds, such compounds have very low vapor pressures. Thus, only insubstantial quantities of riperoxide or trioxolane compounds would be expected to be found in vapor.

Knox, U.S. Pat. No. 1,210,949 discloses ozonation of castor oil in order to produce a laxative. Ozonation of the oil was believed to reduce its toxicity and create a germicidal effect. In order to produce substantial quantities of riperoxide or trioxolane compounds using the method disclosed by Knox, temperatures approaching $-50°$ C. using a very dilute solution would be required.

Johnson, U.S. Pat. No. 2,356,062 discloses the use of ozonides of glycerine trioleates for external application, because it was believed that those particular triglycerides had a germicidal, fungitidal, and deodorizing effect. The methods of Johnson, for reasons described above in connection with the Patent to Knox, are also not believed to result in the production of significant quantities of diperoxide or trioxolane compounds.

DeVillez, U.S. Pat. Nos. 4,451,480 and 4,591,602, discloses use of ozonides of certain fatty acids, including olive oil, sesame oil, jojoba oil, castor oil, and peanut oil, for external use as antimicrobial agents, particularly in the treatment of ache. It is believed that at least some of these compounds cause unacceptable skin irritation. DeVillez discloses ozonation at 35°–65° C., a temperature at which diperoxides and trioxolanes are not expected to be formed in substantial quantities.

Accordingly, so far as can be determined, none of the medical uses of ozonated compounds described in the prior art have ever made use of substantial quantities of trioxolane or diperoxide compounds. Moreover, none of the prior art ozonated compounds appears to have ever been commercialized for medical applications. Presumably, this lack of commercialization is due to unacceptable side-effects, toxicity, difficulties in storage, or minimal effectiveness. Many of these various compositions decompose on standing.

Immunomodulation offers an opportunity to treat a variety of medical conditions. For example, both infections and neoplasms can be treated by increasing the immune response thereto. Some allergic reactions and other auto-immune responses can also be treated through immunomodulation. However, there are few effective immunomodulatory therapies known; and many of the known immunomodulatory therapies produce untoward side effects. Thus, there is a need for safe and effective immunomodulatory treatment.

At any one time, it is estimated that ⅓ of all women are suffering from bacterial or fungal vaginal infection. The only presently available treatments are time consuming and the medications used are irritating to mucous membranes. Thus, there is a need for a relatively non-irritating, safe, and effective composition for treatment of these infections.

Genital herpes lesions and Herpes simplex lesions are notoriously resistant to treatment. These viral infections inflict a significant percentage of the population, and there is, at present, no known cure. Thus, a need exists for compositions that can treat herpes lesions in at least a palliative manner to minimize the discomfort suffered by those suffering from these diseases.

Chicken pox (Herpes zoster) is a common childhood disease, for which no vaccine is currently known. Lesions of chicken pox cause itching, and may lead to permanent disfigurement, if scratched. Since the disease strikes mainly children, who are unable to resist scratching, the need exists for compositions that can anti-pruritically treat chicken pox lesions to minimize disfigurement caused by the disease.

External fungal infections, such as athletes foot and onychomycosis (fungal infections of the nails), afflict a large portion of the human population. Similar fungal infections afflict a large percentage of the animal population. Current treatments for external fungal infections are irritating to sensitive individuals, and not always effective. In addition, onychomycosis is difficult to treat, and its incidence appears to be on the rise with the advent of acrylic and other adhesively-mounted artificial nails. Therefore, a need exists for a relatively non-irritating, effective treatment for these infections.

Indolent neoplasms of the skin, such as warts and moles, also afflict a large portion of the human and animal population. Current over-the-counter medications are not always effective, and the only effective therapy in some instances is to have the neoplasms frozen or burned off, necessitating a doctor's visit. Thus, a need exists for a treatment which is effective, and which can be applied by the patient or owner of the afflicted animal.

Steroidal medications are currently in widespread use to relieve the discomforts of bee stings, insect bites, and other dermatoses, such as those caused by psoriasis, poison oak, or poison ivy. While these medications are sometimes effective, their long term use can result in side effects, including thinning of the skin, sleeplessness, physical deformation, improper fat deposition, dependency, and others. Thus, there is a need for an effective alternative medication for these ailments.

Symptoms of sunburn can range from mild discomfort to severe burns. This condition occasionally affects virtually the entire population. Current treatments do little more than mask the pain associated with this condition. Products which prevent sunburn, when applied prior to exposure, are currently available. However, there is no product currently available which prevents sunburn symptoms or alleviates the severity of sunburn when applied after exposure to the sun. Many people carelessly or inadvertently expose themselves to the sun without using protective sunscreens. Thus, a need exists for a product that can prevent sunburn after exposure to the sun.

In the treatment of severe burns, prevention of dehydration and infection in the burned patient are major concerns. Currently used therapies for severe burns which address these concerns are often irritating to sensitive, burned tissues. Thus, there is a need for a method of treating burns that is non-irritating, yet still effective against both dehydration and infection.

Many adolescents and young adults suffer from acne. Many compounds are currently available to treat ache, with variable effectiveness. The most effective compositions currently known to treat ache use active oxygen to kill the bacteria which are, in part, responsible for the condition. These include benzoyl peroxide. However, these compositions are sometimes irritating, do not always deliver enough oxygen for optimal effectiveness, and can cause drying of the skin. Thus, a need exists for a non-desiccating, effective, and non-irritating treatment for acne.

Sexually transmitted diseases (STDs), including herpes, syphilis, gonorrhea and AIDS, are endemic in today's society. Condoms are currently the most effective means of preventing the transmission of these diseases. However, condoms are not 100% effective. A need, therefore, exists for preparations which increase the effectiveness of condoms in preventing the transmission of STDs.

Both topical and systemic Leishmaniasis are widespread throughout the tropical areas of the world. Presently, at least 4,000,000 people are know to be infected with a parasite which causes one of these conditions. No totally effective therapies are known. Accordingly, a clear need is evident for an effective treatment or therapy for these diseases.

SUMMARY OF THE INVENTION

One aspect of the present invention provides a method of medical treatment for a medical condition in a mammal. The method includes the application to the mammal of a pharmacologically effective amount for treatment of the condition, of a trioxolane or a diperoxide of a non-terpene unsaturated hydrocarbon. The application can advantageously parenteral, topical or other method known to those of ordinary skill in the art. In certain preferred embodiments, the non-terpene unsaturated hydrocarbon is either 3-hexene-1-ol or erucic acid.

Other aspects of the present invention provide a method of modulating the immune system of a mammal, a method of treating bacterial infections in a mammal, a method of treating fungal infections in a mammal, a method of treating protozoal infections in a mammal, a method of treating viral infections in a mammal, and a method of treating inflammation of a tissue in a mammal. Each of these methods includes applying a pharmacologically effective amount of a trioxolane or a diperoxide of a non-terpene unsaturated hydrocarbon to the mammal in an amount effective to produce the desired treatment. These methods can also include hydrolyzing the trioxolane or diperoxide derivative to produce a therapeutic molecule having a therapeutic effect on the mammal. Preferably, this therapeutic molecule comprises a carbonyl zwitterion. A variety of medical conditions can be treated using these methods. For example, HIV infection, fungal diseases of the skin, bacterial diseases of the skin, impetigo, paronychia, viral diseases of the skin (such as herpes infection, venereal warts, and common warts), dermatological conditions (such as eczema, psoriasis, insect bites, coral bums, jellyfish stings, poison oak, seborrheic dermatitis and burns), dental or oral conditions (such as pharyngitis, tooth ache, halitosis, canker sores and gingivitis), and hemorrhoids can all be treated with these methods. The non-terpene unsaturated hydrocarbon used in these methods can be any of a number of such compounds, such as erucic acid or 3-hexene-1-ol.

The present invention also includes pharmaceutical compositions for the treatment of a medical condition in a mammal. These compositions include a pharmaceutically effective amount for treatment of the condition, of a trioxolane or a diperoxide of a non-terpene unsaturated hydrocarbon in a pharmaceutically acceptable, non-aqueous carrier. Certain preferred forms of these compositions are toothpaste, mouthwash, rectal or vaginal suppositories, topical preparations, and forms suitable for sublingual application or parenteral administration. The composition can also be applied to a condom or be made in combination with soap.

Another aspect of the present invention provides a method of preventing sexually transmitted infections or preventing pregnancy in a mammal. This method includes application to the genitals of the mammal of a trioxolane or diperoxide derivative of an unsaturated hydrocarbon.

Still another aspect of the present invention provides a method of treating cancer in a mammal having cancer, comprising the application to the mammal of a pharmacologically effective amount for treatment of cancer, of a trioxolane or a diperoxide of a non-terpene unsaturated hydrocarbon. In certain preferred embodiments of this method the method is used to treat a mammal that has a cancer such as adenocarcinoma of the lung, Hodgkin's Disease, or lymphoma.

The present invention also includes a method of treating rheumatoid arthritis, osteoarthritis or inflammatory polyarthritis in a mammal. This method includes identifying a mammal having one of the conditions, and applying a trioxolane or a diperoxide of an unsaturated hydrocarbon to the mammal.

Still other aspects of the present invention provide methods of treating topical or systemic leishmaniasis, chronic fatigue syndrome or lupus erythematosus in a mammal. These methods include identifying a mammal having the indicated condition and applying a trioxolane or a diperoxide of an unsaturated hydrocarbon to the mammal. In a similar aspect of the invention, there is provided a method of treating a physical wound to a tissue of a mammal. This aspect of the invention includes identifying a mammal having a wound to a tissue thereof, and applying a trioxolane or a diperoxide of an unsaturated hydrocarbon to the tissue. This method can also include preventing scar formation through application of a trioxolane or a diperoxide of an unsaturated hydrocarbon to the tissue.

DETAILED DESCRIPTION OF THE INVENTION

Unsaturated Hydrocarbon Starting Materials

Terpene hydrocarbons are also known as isoprenoids, because they may generally be constructed from isoprene units (C—C=C—C=C). Thus, terpene hydrocarbons are usually exact multiples of $C_5H_8$. Terpenes are classified according to the number of isoprene units of which they are composed, as shown in Table 1.

TABLE 1

| 1 hemi- | 5 ses- |
|---------|--------|
| 2 mono- | 6 tri- |
| 3 sesqui- | 8 tetra- |
| 4 di- | n poly- |

While not limiting the scope of the invention, examples of terpenes which can prove especially effective, when used in certain preferred methods of the present invention include limonene, citronella, alpha-carotene, beta-carotene, Vitamin A, linalool, linalyl acetate, and squalene. Other compounds which are believed to make pharmacologically active terpene trioxolane or diperoxide derivatives in accordance with the present invention include geraniol, limonene, alpha-pinene, loganin, cymene, farnesanes, eudesmanes, acoranes, cedranes, chamigranes, caryophyllanes, illudanes, humulenes, himachalenes, longifolanes, perhydroazulenes, quaianes, quaianolides, and germacranes. Still other compounds which are believed to make pharmacologically active terpene trioxolane or diperoxide derivatives in accordance with the present invention include labdanes, clerodanes, abietic acid, phyllocladene, giberellins, ophiobolin A, retigeranic acid, gasgardic acid, lanosterol, euphol, oleanane, ursane, lupeol, hydroxyhopanone, lupanes, and hopanes. Other particular terpene compounds which are believed to make pharmacologically active terpene trioxolane or diperoxide derivatives when prepared in accordance with the present invention include B-selinene, zingibene, camphene, sabinene, ocimene, myrcene, nerol, citral A, citral B, farnesol, bisabolene, phytol, and cecropia hormone. Trioxolane or diperoxide derivatives of terpenes have three or four oxygen atoms respectively replacing the double bonds at sites of unsaturation, creating a trioxyacydopentane referred to herein as a trioxolane derivative. We have now discovered that pharmacologically active compounds can be produced through ozonation of both terpene and non-terpene unsaturated hydrocarbons under conditions which lead to the formation of substantial quantities of trioxolane or diperoxide derivatives thereof.

Methods of Synthesis

In the preparation of trioxolane and diperoxide derivatives, the particular terpene or non-terpene unsaturated hydrocarbon starting material is first obtained. A large and representative number of terpene and non-terpene unsaturated hydrocarbon starting material compounds are disclosed in the literature and/or are commercially available.

In the trioxolane or diperoxide compound synthesis, ozone is passed through the unsaturated hydrocarbon starting material under conditions that provide for intimate contact between the starting material and the ozone, such as thin film procedures,' sparging, gas entrainment procedures, and the like. On a small scale, for example, the unsaturated hydrocarbon is placed in a vented vessel, and ozone is sparged through the material until the reaction is complete.

Trioxolane derivatives are generally favored in the ozonation of unsaturated hydrocarbons. However, diperoxide derivatives are generally produced from trans isomers of asymmetric compounds and from hydrocarbon compounds having sites of unsaturation including a tertiary carbon. When compounds which tend to produce diperoxide derivatives are used in the ozonation reaction, slightly higher temperatures can be tolerated in order to produce the diperoxides. Thus, these compounds can be ozonated at temperatures up to 35° C. The ozonation of compounds which tend to produce trioxolane derivatives should generally be undertaken at temperatures less than 25° C. in order to produce substantial quantities of the derivatives.

It is important to use a proper combination of solvent and temperature in order to generate substantial quantities of trioxolane or diperoxide derivatives. For generation of substantial quantities, it is generally important to dissolve the starting material in a nonpolar solvent.

Preferably, the starting material is present in a concentration of 3M or less, and more preferably, in a concentration of 0.01M to 1M. Also, as stated above, temperatures below 35° C. are generally required. More preferably, the temperature used with highly non-polar solvents, such as hexane, pentane, or chloroform, is in the range from −150° C. to +25° C. Still more preferably, the temperature used is in the range from −78° C. to −30° C.

The ozone may advantageously be generated with any of the commercially-available ozone generators. Such devices include corona discharge tubes through which oxygen gas may be passed. For example, pure oxygen gas passing through an ozone generator will typically leave the device as from 2% to 6% $O_3$ (ozone), with the remainder $O_2$. This ozone mixture may then be sparged through the terpene or non-terpene unsaturated hydrocarbon starting material at a preferred temperature until the reaction is complete. Completion may be judged by analyzing the gas exiting the ozonation chamber for ozone. (This may be done by passing the exit gas through aqueous potassium iodide and determining whether iodine gas is liberated, or by any other conventional technique.) Alternatively, the reaction may be followed by observing the weight gain of the material undergoing the reaction, by observing changes in physical characteristics (such as conversion from a liquid form to a soft paste), or by simply calculating the quantity of ozone needed to fully ozonate the material and stopping the reaction when a slight excess of ozone has passed through the reaction chamber.

When the starting material is normally a solid, such as β-carotene, it may be solubilized in any suitable saturated nonaqueous solvent system prior to ozonation. With all of the diperoxide and trioxolane compounds, it is desirable to exclude water, lower alcohols, nucleophilic peroxides, and proton donors from the reaction mixture and from the final composition, in order to prevent premature hydrolysis of the trioxolane or diperoxide structure.

The following example shows a representative protocol for production of trioxolane and diperoxide derivatives of unsaturated hydrocarbons.

EXAMPLE 1

Protocol for Production of Trioxolane and Diperoxide Derivatives

Ozone was prepared with an ozone generator. Dry oxygen containing about 10% ozone was introduced at a speed of 10–20 liters/hour in an unsaturated hydrocarbon solution. This solution consisted of the cis isomer of the hydrocarbon in dry and olefin free butane, pentane or n-hexane as solvent. After ozonation, the solvent was removed at 30° C. under rotation. The residue was either distilled/n vacuo or purified by column chromatography on silica gel. The results for various unsaturated hydrocarbons of the general structure RCH=CHR' are shown in Table 2.

TABLE 2

| R | R' | Solvent | Conc. (M) | T (°C.) | Yield (%) |
|---|---|---|---|---|---|
| t-butyl | t-butyl | pentane | 0.3 | −75 | 82 |
| isopropyl | isopropyl | pentane | 1.0 | −70 | 85 |
| ethyl | ethyl | pentane | 0.2 | −30 | 88 |
| methyl | methyl | butane | 0.2 | −30 | 72 |
| isopropyl | methyl | pentane | 1.0 | −70 | 86 |
| ethyl | methyl | pentane | 1.0 | −70 | 91 |
| propyl | methyl | pentane | 1.0 | −70 | 92 |

TABLE 2-continued

| R | R' | Solvent | Conc. (M) | T (°C.) | Yield (%) |
|---|---|---|---|---|---|
| t-butyl | methyl | pentane | 1.0 | −70 | 81 |
| t-butyl | ethyl | pentane | 1.0 | −70 | 84 |

In addition to compounds of the structure RCH=CHR', we have also subjected cycloöefins to ozonation using the general protocol of Example 1. Such cycloöefins can be ozonated at a concentration of 3.0M in n-hexane at −70° C. to produce a yield of approximately 96%. However, the product of ozonation of cycloöefins tends to be peroxide derivatives and/or insoluble polymers of trioxolanes in inactive solvents, such as pentane. Soluble trioxolane compounds can be formed from cycloölefins using active solvents such as ethyl acetate or acetone. The active solvent will enter into the resulting trioxolane composition to produce a soluble monomer.

Acyclic conjugated dienes and other polyunsaturated hydrocarbons can also be ozonated to yield pharmaceutically active compounds for use within the scope of the present invention. For example, acyclic conjugated dienes can be dissolved in pentane at 0.8M at a temperature of −780° C. to produce a yield of approximately 74%.

Procedures other than ozonation are also known which can result in the production of either the trioxolane or diperoxide derivatives. For example, non-ozonation procedures for the production of methyl ethyl ketone diperoxide, diethyl ketone diperoxide, 1,1-dimethyl-4,4-diethyl-2,3,4,5-tetroxacyclohexane and 1,4,4-trimethyl-1-ethyl2,3,5,6-tetraoxacyclohexane are described in Murray et at., supra.

EXAMPLE 2

Examination of Conditions for Production of Trioxolane and Diperoxide Derivatives The ozonation protocol of DeVillez (U.S. Pat. No. 4,451,480) and that of Example 1 were each used on a sample of erucic acid methyl ester (a non-terpene unsaturated hydrocarbon) and on a sample of jojoba oil (a terpene unsaturated hydrocarbon). In the DeVillez protocol neat samples were ozonated at ambient temperature (approximately 20° C.). In the Example 1 protocol, 3% samples in chloroform were ozonated at −30° C. Trioxolanes and diperoxides have a greater dipole moment than the unozonated compounds which substantially increases their retardation factor ($R_f$) upon chromatography. Thus, after ozonation, all four samples and a sample of each of the unozonated compounds were chromatographed according to the method described by DeVillez using chloroform as a mobile phase and high performance silica gel as the stationary phase. The resulting plates were charred with iodine for identification. The results are shown in Table 3

TABLE 3

| Compound | $R_f$ |
|---|---|
| Unozonated Erucic Acid Methyl Ester | 0.9 |
| Ozonated Erucic Acid Methyl Ester (DeVillez) | 0.8, 0.9 |
| Ozonated Erucic Acid Methyl Ester (Example 1) | 0.4, 0.5 |
| Unozonated Jojoba Oil | 0.6 |
| Ozonated Jojoba Oil (DeVillez) | 0.5, 0.6 |
| Ozonated Jojoba Oil (Example 1) | 0.1, 0.2 |

It can be seen from the results in Table 3 that the method of DeVillez results in the formation of two spots upon chromatography, one of which appears to have the same $R_f$ as the unozonated compound, and the other of which is only slightly retarded. These two spots are believed to represent the unreacted compound and a peroxide derivative thereof (R—C—O—O—C—R'). In contrast, the method of Example 1 results in the formation of two spots, both of which are greatly retarded from the unozonated compound. These two compounds are believed to represent the trioxolane and diperoxide derivatives of the compounds.

Pharmaceutical Compositions

In one preferred embodiment of the present invention, the compounds of the present invention are formulated into pharmaceutical preparations. These pharmaceutical preparations include one or more of the trioxolane or diperoxide derivative compounds of the present invention, and may further include other pharmaceutically active ingredients. In addition, any of the well-known pharmaceutically-acceptable carriers or excipients may be combined with the compounds of the present invention in a well-known manner. Suitable diluents include, for example, polyethylene glycol isopropyl myristate, and mineral oil. The pharmaceutical composition may be in any form suitable for topical use, such as an ointment, gel, or cream. Conventional coloring, fragrance and preserving agents may also be provided.

The excellent weight to oxygen ratio of some of the trioxolane or diperoxide derivatives of unsaturated hydrocarbons renders them especially effective in treating many medical conditions. Trioxolane or diperoxide derivatives of highly unsaturated hydrocarbons are capable of releasing large amounts of oxygen, up to 30% of the weight of the compound and more. The trioxolane derivatives have three oxygen atoms at each site of unsaturation, while the diperoxide derivatives have four oxygen atoms. In addition, the trioxolane and diperoxide derivatives used in the present invention appear to have significant unexpected pharmacological properties that are different in kind or quality from those of unrelated ozonated compounds disclosed in the prior art.

The effective dosage of the compounds of the present invention appears to be much lower than would be expected in light of the prior art, suggesting that the compounds have unexpectedly high efficacy. While the compounds may be used neat (and, indeed, some of them form pharmaceutically elegant creams or ointments, e.g., linalyl trioxolane or diperoxide derivative and linalool trioxolane or diperoxide derivative), the effective concentration for most topical applications can be as little as 0.01%, by weight. However, the compositions more preferably contain from about 0.5% or 1% to about 10% or 20% by weight active ingredient. Topical compositions containing about 2% or 3% of active ingredient appear to be particularly effective.

For systemic use, such as intravenous, intramuscular, or intraperitoneal injection, as well as rectal suppositories, the compositions may similarly contain from about 0.01% to about 99% active ingredient, by weight. Preferred systemic compositions contain from about 0.05% to about 20% active ingredient, by weight.

The present invention further includes other suitable pharmacological preparations of trioxolane or diperoxide derivatives including: medicinal douches, eardrops, eyedrops, throat sprays, sublingual preparations, dental preparations for topical sores, mouthwashes, toothpaste, armpit deodorants, disinfectant/germicidals, germicidal soaps, and contact lens sterilization solutions. In addition, in certain embodiments of the invention, the trioxolane or diperoxide derivatives are applied to a condom.

Thus, Example 3-9 are provided to illustrate certain pharmaceutical compositions within the scope of the present invention. As such, these examples are not intended to limit the invention.

EXAMPLE 3

A vaginal Suppository for Treatment of Vaginitis

| A vaginal suppository for treatment of vaginitis | |
|---|---|
| 2% w/v | Ozonated linalyl acetate, from Example 2 |
| Balance | Hydrogenated vegetable oil base |

EXAMPLE 4

A topical Gel Effective Against Burns

| A topical gel effective against burns | |
|---|---|
| 1% w/v | Geraniol trioxolane |
| 60% w/v | Carbomer 934 |
| 1% w/v | Disodium edetate |
| 10% w/v | Glycerin |
| Balance | Polyethylene glycol m.w. 400 |

EXAMPLE 5

A Toothpaste Effective Against Gingivitis

| A toothpaste effective against gingivitis | |
|---|---|
| 1% w/v | Trioxolane derivative of cis 3-hexene-1-ol |
| Balance | Conventional toothpaste formulation |

EXAMPLE 6

A Topical Cream Effective Against Acne

| A topical cream effective against acne | |
|---|---|
| 2.5% w/v | Linalool trioxolane |
| 48% w/v | Propylene glycol |
| 30% w/v | Propyl paraben |
| 5% w/v | Polysorbate 60 |
| 10% w/v | Glyceryl monostearate |
| Balance | Mineral oil |

EXAMPLE 7

A Lubricant for Condoms Effective Against the Transmission of STDs

| A lubricant for condoms effective against the transmission of STDs | |
|---|---|
| 0.2 g/ml | Ozonated erucic acid |
| 10% w/v | Glyceryl stearate |
| 1% w/v | Food-starch modified |
| 2% w/v | Polyethylene glycol mw. 800 |
| balance | Light mineral oil |

EXAMPLE 8

An Injectable Composition Effective Against Verrucae

| An injectable composition effective against verrucae | |
| --- | --- |
| 25 mg/ml | ozonated linalyl acetate from Example 2 |
| balance | Polyethylene glycol mw. 200 |

EXAMPLE 9

A Rectal Suppository Effective Against Systemic Disorders

| A rectal suppositoxy effective against systemic disorders | |
| --- | --- |
| 250 mg/ml | Trioxolane derivative of cis 3-hexene-1-ol |
| 2 ml | Pluracols (a mixture of high molecular weight polyethylene glycol) |

EXAMPLE 10

A Rectal Suppository Effective Against Systemic Disorders

| A rectal suppository effective against systemic disorders | |
| --- | --- |
| 250 mg | Geraniol Trioxolane |
| 1.5 ml | Cocoa butter with bees' wax |

The toxicity of the trioxolane and diperoxide derivatives appears to be surprisingly low, in both topical and systemic use. Our preliminary data suggest that the $LD_{50}$ for a representative compound, linalool trioxolane is about 3000 mg/kg in mice.

We have discovered that the trioxolane and diperoxide derivatives of terpene and non-terpene unsaturated hydrocarbons of the present invention, when applied topically in suitable pharmacological compositions, are effective for treatment of bacterial, vital, protozoal and fungal infections and for treatment of a variety of inflammatory conditions.

In this regard, we have discovered that topical administration of the trioxolane or diperoxide derivatives of the present invention, in a suitable composition having from about 0.1% to about 50% active ingredient by weight, preferably about 0.5% to about 20% by weight, is effective to minimize the extent and severity of Herpes simplex, genital herpes, and chicken pox lesions, when applied on incipient eruptions.

We have also discovered that vaginal administration of a composition containing the trioxolane or diperoxide derivatives of the present invention, in a suitable vaginal carrier (such as a suppository, cream, gel, or foam) having from about 0.05% to about 90% active ingredient, by weight, preferably about 0.1% to about 20% by weight, is substantially non-irritating to mucous membrane tissues, and is effective to treat both bacterial and fungal vaginal infections.

Furthermore, we have discovered that topical administration of the trioxolane or diperoxide derivatives of the present invention, in a suitable composition having from about 0.01% to about 99% or 100% active ingredient, by weight, preferably from about 0.1% to about 25% by weight, is effective in treating fungal infections of the skin and nails, such as athlete's foot and onychomycosis. Similar compositions appear to have a shrinking effect on indolent neoplasms, including warts and moles.

Compositions having from about 0.01% to about 50% active ingredient, preferably about 0.1% to about 20%, are non-irritating to ache affected skin, and have exhibited a strong anti-comedonal effect when used topically on affected areas. It is believed that these compositions deliver nascent oxygen to kill anaerobic bacteria such as P. ache when the trioxolane or diperoxide derivatives undergo hydrolysis. Furthermore, while it is not intended that the applicants be limited to any particular theory or mode of action, it is further believed that the particular ozonolysis fragments (such as ketones or carboxylic acids) formed by trioxolane or diperoxide derivatives upon release of oxygen have a complimentary pharmacological effect.

Moreover, our data further indicate that topical application of the trioxolane or diperoxide derivatives of the present invention, after significant exposure to the ultraviolet component of sunlight, is effective in ameliorating the severity of sunburn and facilitating the healing process. Similar reduction of pain, inflammation, and blistering, and an increase in the speed of the healing process has been observed when the composition of the present invention is applied to first and second degree thermal burns on a mammal.

Based on the demonstrated antiviral, antifungal, and antibacterial properties of the present compositions in vitro, and the relatively non-irritating properties of the trioxolane or diperoxide derivatives, it is further believed that topical administration of the compounds of the present invention can decrease the probability of transmission of sexually transmitted diseases (STD's). Thus, for example, the previously described vaginal compositions may be used alone or in conjunction with a condom to decrease the risk of infection. In this regard, the active ingredient may further advantageously be formulated into a lubricating composition of known type.

Furthermore, we have discovered that the trioxolane and diperoxide derivatives of the present invention are effective spermicides. Thus, intravaginal application thereof can serve to minimize the chances of pregnancy as well as to prevent the transmission of STD's.

We have also discovered that topical administration of trioxolane or diperoxide derivatives in a topical preparation exhibits significant efficacy in the treatment of most dermatoses, including psoriasis and those dermatoses caused by bee stings, insect bites, poison plants such as poison oak, poison ivy, and stinging nettle, diaper rash, hives, and other reactions for which antihistamine or steroidal medications are commonly prescribed. Administration of the trioxolane or diperoxide derivatives of the present invention in lieu of steroids medications is sometimes equally effective; however, side effects are considerably reduced, making therapy with trioxolane or diperoxide derivatives the more desirable treatment. The invention, however, contemplates combination therapy in some instances. Thus, in addition to an effective amount of trioxolane or diperoxide derivative, the compositions of the present invention may further include an effective amount of an antihistamine or a corticosteroid. These medications are well known, and effective dosages for the various antihistamines and corticosteroids have been established. When used together with a trioxolane or diperoxide derivative, the effective topical concentrations of these ingredients will generally be toward the lower end of the effective range in which they are presently used alone.

The present invention also includes methods of systemic and localized injection of the compositions disclosed herein, including intravascular, intramuscular, subcutaneous, intraperitoneal, and other injection techniques. Such injection may be used for treatment of viral, fungal, and bacterial infection. We have also discovered that localized injection of a trioxolane or diperoxide derivative of the present invention into a tumor has an anti-neoplastic effect.

EXAMPLE 10

Test For Efficacy Of Treatment of Sunburn

The composition of Example 4 is applied topically to only a portion of the skin surface of a severely sunburned patient in a single application, two hours after the exposure to sunlight. The treated area exhibits slight reddening, but no peeling or blistering. Only minor discomfort is apparent. The untreated area, in contrast, becomes red, blistered, and painful.

EXAMPLE 11

Test for Efficacy of Treatment of Chicken Pox

The composition of Example 6 is topically applied to a portion of the lesions on a child suffering from chicken pox. Within 1 hour, the treated lesions are significantly reduced with little or no self-induced trauma from scratching. The untreated lesions are unchanged in size, and show the effects of trauma from scratching.

EXAMPLE 12

Test For Efficacy of Treatment of Swollen Joints

Patients at a sports medicine clinic complaining of swollen knees are divided into three groups: groups A, B and C. The patients in group A receive an injection of the composition of Example 8 into the swollen knee. The patients in group B receive an injection of a placebo, the composition without active ingredient. The patients in group C receive an injection of a corticosteroidal medication. Within 12 hours the swelling in the knees of the patients in group A is significantly reduced. No change is reported in the knees of the patients of group B. The swelling in the knees of the patients of group C is also reduced, however, a significant percentage of the patients suffer inflammatory reactions.

EXAMPLE 13

Test For Efficacy of Treatment of Fungal Infections of the Vagina

The suppository of Example 3 is administered intravaginally to one group of patients suffering from yeast infections of the vagina. A second group of such patients receive a suppository without the active ingredient of Example 3. A third group receives a suppository containing the drug clotrimazole, a commonly used drug for treatment of fungal infections of the vagina. Every 24 hours the process is repeated. Within 2 days, the patients of the first group have no reddening of the vagina and within 7 days, a yeast culture produces negative results. The second group of patients continues to complain of itching and other common complaints of fungal infections. A yeast assay is positive. For patients in the third group, a yeast assay is negative; however, a number of these patients complain of irritation and in those patients, a significant reddening of the vagina is present.

EXAMPLE 14

In Vitro Anti-Microbial Assay of Linalool Trioxolane

A culture of $E.coli$ was harvested with sterile saline using swabs. The number of Colony Forming Units (CFUs) per ml in the suspension was determined by Standard Plate Count Method. A working suspension of $E.\ coli$ with approximately $1.0 \times 10^7$ CFUs/ 0.1 ml was then prepared. Four aliquots of 1 ml of test ointment containing 1.0% trioxolane or diperoxide derivative of linalool were removed and place in separate sterile screw-capped tubes. Each sample was inoculated with 0.1 ml of the working suspension of $E.\ coli$ to yield a final concentration of approximately $1 \times 10^6$ CFUs/1 ml of the product. The samples were stored at 20°-25° C. for a total of 28 days. Samples were selected at 7 day intervals to determine the number of viable CFUs present. A control with uninoculated ointment was also stored with samples selected at the same intervals. At 7 days, and all subsequent sample selections, there were less than 10 CFUs present. No CFUs were present in any control sample.

EXAMPLE 15

Primary Skin Irritation Test of Trioxolane or Diperoxide Derivative of Linalool

Six healthy New Zealand White rabbits were tested for skin irritation. Approximately four hours prior to application of the trioxolane or diperoxide derivative sample, the backs of the animals were clipped free of fur. Each rabbit received epidermal abrasions with a sterile needle at one test site while the skin at another test site remained intact. A 1.0% solution of linalool trioxolane or diperoxide derivative in isopropyl myristate was prepared. A 0.5 ml portion of the test solution was applied to each site by introduction under a double gauze layer to an area of skin approximately 1" square. The patches were covered with a nonreactive tape and the entire test site was wrapped with a binder. After 24 hours, the binders, tape, and test material were removed and the skin evaluated. The test material residue was removed with 70% isopropyl alcohol. An evaluation was also made at 72 hours after application. The reactions were scored according to the methods described in the Federal Hazardous Substances Act. The test solution had a Primary Irritation Index (PII) of 1.0. According to FHSA regulations, a material with a PII of less than 5.00 is generally not considered a primary irritant to the skin.

EXAMPLE 16

Ocular Irritation Test in the Rabbit of Linalool Trioxolane

Six healthy New Zealand White rabbits were selected for study. The rabbits' eyes were judged free of irritation prior to the study by examining with a pen light and under UV light after installation of 2% fluorescein stain. A 1% solution of the trioxolane or diperoxide derivative of linalool was prepared in isopropyl myristate. A 0.1 ml portion of this test solution was instilled into the lower conjunctival sac of one eye of each rabbit. The lids were held dosed for one second. The opposite eye of each rabbit received 0.1 ml of the isopropyl myristate, as control. Eyes were examined and the ocular reaction scored according to the "Illustrated Guide for Grading Eye Irritation by Hazardous Substances" (Appendix 1). At 24, 48, and 72 hours post dosing, the eyes were examined with a pen light and re-examined with UV light following fluorescein staining of the cornea. Under the conditions of this test, the test solution was considered a non-irritant to ocular tissues of the rabbit.

Studies on Derivatives of is Terpene and Non-Terpene Unsaturated Hydrocarbon

1. INTRODUCTION

Geraniol trioxolane, a trioxolane derivative of a terpene, was assessed on the basis of its direct biological activity against certain target organisms in vitro. In vivo assays were similarly undertaken to assess the product's toxicity, safety, and in certain cases, efficacy. The studies were conducted using product manufactured using the synthesis protocol of Example 1, and synthesized strictly in accordance with international guidelines and specifications, especially those issued by Untied States Food and Drug Administration, United States Pharmacopoeia, British Pharmacopoeia, Kenya Association of Manufacturers, and Pharmacy and Poisons Board of Kenya. The preparatory process met aH requirements for the Code of Good Manufacturing Practices (GMP). In addition, the trioxolane derivative of cis 3-hexene-1-ol, a non-terpene, was synthesized and compared to Geraniol trioxolane for the purposes of assessing its comparative activity.

Both Geraniol trioxolane and the trioxolane derivative of cis 3-hexene-1-ol are colorless liquids. Geraniol trioxolane is more viscous and less stable than the trioxolane derivative of cis 3-hexene-11 -ol.

2. IN VITRO EXPERIMENTAL STUDIES 2.1 Effect of Geraniol trioxolane and the trioxolane derivative of cis 3-hexene-1-ol on *Leishmania donovani* and *Leishmania major* promastigotes in vitro 2.1.1 Geraniol trioxolane This was first diluted in PEG600 to give 250 mg/ml, and further diluted in culture medium to give a working concentration of 62.5 mg/ml. Through serial dilutions, the compound showed killing of all promastigotes up to a dilution 1:2048 within 18 hours. The controls in the same titre plate survived.

2.1.2 Trioxolane derivative of cis 3-hexene-1-ol

This compound was first diluted to 400 mg/ml in PEG600, and further serially diluted in culture medium. The compound caused the killing of all promastigotes within 18 hours up to a dilution of $1:2^8-2^9$.

2.2 Effect of Geraniol trioxolane and the trioxolane derivative of cis 3-hexene-1-ol on myeloma cell line and spermatozoa The susceptibility of Myeloma cell line (x63 balb/c line) and human spermatozoa to both Geraniol trioxolane and the trioxolane derivative of cis 3-hexene-1-ol was assessed. The myeloma cell line was killed within 48 hours and human spermatozoa were killed within 1 minute, at dilutions of less than $1:2 \times 10^{10}$ of the working concentrations.

2.3 Effect of Geraniol trioxolane and the trioxolane derivative of cis 3-hexene-1-ol on microörganisms It was decided to test the direct biological activity of both Geraniol trioxolane and the trioxolane derivative of cis 3-hexene-1-ol on microörganisms which cause common infections in our community. Thus, the following microörganisms were tested for their susceptibility to these compounds:

2.3.1 Diarrhoeal diseases
  i) Salmonella spp.
  ii) Shigella spp.
  iii) Enteropathogenic/enterotoxigenic *Escherichia coli*

2.3.2 Urinary tract infections: both bacteria and fungi
  i) *Neisseria gonorrhoea* (PPNG and non-PPNG)
  ii) *Candida albicans*
  iii) Pseudomonas spp.

2.3.3 Bacteria causing respiratory tract infections
  i) Klebsiella spp.
  ii) *Staphylococcus aureus*
  iii) *Staphylococcus epidermidis*

2.3.4 Other infections caused by bacteria
  i) Proteus
  ii) Achromobacter
  iii) *E. coli*

2.3.5 Fungal infection
  i) Common dematophytes
    a) *Trichophyton violaceurn*
    b) *Trichophyton canis*
  ii) Systemic fungi
    a) Cryptoccus spp.
    b) Candida spp.
  iii) Other general fungi
    a) *Phialophora verrucose*
    b) *Penicillium* spp.

2.4 Results

Minimum inhibition concentration (MIC), as well as minimum bacterial concentration (MBC), of the drugs on the common pathogens were determined. Standard drugs, and in certain cases reference stains, were used as controls and for comparative purposes. Results of observations are summarized in Tables 4-6.

TABLE 5

MIC of Geraniol trioxolane and the trioxolane derivative of cis 3-hexene-1-ol on some common pathogens in agar dilution

| | | MIC (mg/ml) | | |
| | | Geraniol trioxolane | | Trioxolane derivative of cis 3-hexene-1-ol |
| Organism | N | agar | broth | agar | broth |
|---|---|---|---|---|---|
| S. aureus | 10 | 0.15 | 0.78 | 0.12 | 0.62 |
| EPEC/ETEC | 5 | 0.62 | 0.56 | 0.031 | 0.62 |
| Salmonella | 3 | 0.31 | 3.12 | 0.007 | 0.15 |
| Shigella | 7 | 0.31 | 1.56 | 0.007 | 0.62 |
| Pseudomonas | 2 | 0.035 | 1.56 | 0.007 | 0.62 |
| Candida | 2 | 0.62 | 3.12 | 0.031 | 0.31 |

Note:
* numbers in parentheses indicate the lowest concentration inhibiting at least one isolate of organisms
N = number of isolates tested
MIC = minimum inhibition concentration
EPEC/ETEC = enteropathogenic *Escherichia coli*/enterotoxigenic *Escherichia coli*

TABLE 4

MIC of Geraniol trioxolane and the trioxolane derivative of cis 3-hexene-1-ol on various common pathogens by agar diffusion method

| | | MIC (mg/ml) | |
| Organism | N | Geraniol trioxolane | Trioxolane derivative of cis 3-hexene-1-ol |
|---|---|---|---|
| Gram positive cocci | | | |
| S. aureus | 16 | 0.31 (0.004)* | 0.25 (0.031) |
| S. epidermidis | 14 | 0.31 (0.004) | 0.025 (0.031) |
| Gram negative cocci | | | |
| N. gonorrhoea | 49 | 0.15 (0.008) | 0.0035 (0.0019) |

TABLE 4-continued

MIC of Geraniol trioxolane and the trioxolane derivative of cis 3-hexene-1-ol on various common pathogens by agar diffusion method

| Organism | N | Geraniol trioxolane | Trioxolane derivative of cis 3-hexene-1-ol |
|---|---|---|---|
| Gram negative bacilli | | | |
| Salmonella | 3 | 0.31 | 0.007 |
| Shigella | 7 | 0.31 | 0.25 (0.031) |
| EPEC/ETEC | 16 | 0.52 (0.31) | 0.25 (0.031) |
| Pseudomonas | 2 | 0.035 | 0.007 |
| Klebisella | 1 | 0.017 | 0.007 |
| E. coli | 3 | 0.31 | 0.12 |
| Archromobacter | 1 | 0.62 | 0.06 |
| Fungi | | | |
| C. albicans | 5 | 0.62 | 0.031 |
| Tri. violaceum | 1 | 0.31 | 0.15 |
| Tri. canis | 1 | 0.31 | 0.15 |
| Cryptococcus | 1 | 0.15 | 0.015 |
| Ph. verrucose | 1 | 0.31 | 0.15 |
| Penicillium | 1 | 0.62 | 0.31 |

Note:
*numbers in parentheses indicate the lowest concentration inhibiting at least one isolate of organisms
N = number of isolates tested
MIC = minimum inhibition concentration
EPEC/ETEC = enteropathogenic Escherichia coli/enterotoxigenic Escherichia coli

TABLE 6

MBC of Geraniol trioxolane and the trioxolane derivative of cis 3-hexene-1-ol on various common pathogens by broth method

| Organism | N | Geraniol trioxolane | Trioxolane derivative of cis 3-hexene-1-ol |
|---|---|---|---|
| Gram positive cocci | | | |
| S. aureus | 10 | 3.12 (0.78)* | 1.25 |
| S. epidermidis | | | |
| Gram negative bacilli | | | |
| Salmonella | 3 | 6.25 | 2.5 |
| Shigella | 7 | 3.12 | 1.25 |
| EPEC/ETEC | 5 | 3.12 | 1.25 |
| Pseudomonas | 2 | 3.12 | 1.25 |
| Fungi | | | |
| Candida | 2 | 3.12 | 1.25 |

Note:
*numbers in parentheses indicate the lowest bacterial concentration for corresponding organism
N = number of isolates tested
MBC = minimum bacterial concentration
EPEC/ETEC = enteropathogenic Escherichia coli/enterotoxigenic Escherichia coli It can be seen from the results summarized in Tables 4–6 that both Geraniol trioxolane and the trioxolane derivative of cis 3-hexene-1-ol are more active than conventional drugs against commonly encountered microörganisms (in vitro). Thus, the derivatives were found effective against the following microörganisms which cause common infections:

a) diarrhea (Salmonella spp., Shigella spp., enteropathogenic/enterotoxigenic Escherichia coli)
b) urinary tract infections (Neisseria gonorrhoea, candida spp.)
c) respiratory tract infections (Klebsiella spp., Staphylococcus spp.)
d) fungal infections (Trichophyton spp., crytococcus spp., Phialophora spp., Penicillium spp.).

The diluent, propylene glycol, did not inhibit the growth of either bacteria or fungi. Water significantly reduces the direct bioactivity of both Geraniol trioxolane and the trioxolane derivative of cis 3-hexene-1-ol. In comparison, 100% propylene glycol is a better diluent than water.

The trioxolane derivative of cis 3-hexene-1-ol appears to be more active than Geraniol trioxolane, and the direct bioactivity of these drugs were better in agar than in broth methods. However, the activity of both compounds on microörganisms has no relationship with resistance and sensitivity of conventional antibiotics on bacteria. All the microörganisms tested (including both gram positive and gram negative bacteria) were uniformly sensitive to the two products.

3. IN VIVO EXPERIMENTAL STUDIES 3.1 Tolerability of mice to Geraniol trioxolane and the trioxolane derivative of cis 3-hexene-1-ol 20g balb/c mice received various concentrations of both Geraniol trioxolane and the trioxolane derivative of cis 3-hexene-1-ol intraperitoneally (IP). The minimum lethal dose was observed at 3g/kg. Studies on LD50 revealed that the products are highly tolerated.

3.2 Immunomodulatory Activity. of Geraniol trioxolane and the trioxolane derivative of cis 3-hexene-1-ol A group of 15 Balb/c mice which had been used as controls in the previous experiments on Leishmania infection were studied further to assess the activity of both Geraniol trioxolane and the trioxolane derivative of cis 3-hexene-1-ol in the immunological status of these mice.

Bone marrow examination revealed that there was an increase in new clones of lymphocytes in mice put on either Geraniol trioxolane or the trioxolane derivative of cis 3-hexene-1-ol as compared to mice without any drug. This observation strongly suggests that both Geraniol trioxolane and the trioxolane derivative of cis 3-hexene-1-ol are immunomodulators, a property which is of critical consideration in the treatment of diseases that are associated with immunosuppression.

3.3 Treatment of mice infected with Leishmania major

Efficacy of Geraniol trioxolane and the trioxolane derivative of cis 3-hexene-1-ol in the treatment of cutaneous leishmaniasis was assessed in balb/c mice experimentally infected with Leishmania major. The compounds were used intraperitoneally (IP) and topically, and further compared to the standard anti-leishmanial regimen (Pentostam, an antimony-based formulation) and controls.

The topical preparation was formulated as an ointment containing 4 mg/ml of compound and using 0.1 ml per lesion per mouse, whereas the IP preparation contained 0.4 mg in 0.5 ml of compound per mouse. There were a total of 15 mice per treatment group.

The summary of observations is given in Table 7. It is clear that mice treated with the topical preparation responded better than those in any of the other treatment groups.

TABLE 7

Efficacy of Geraniol trioxolane, the trioxolane derivative of cis 3-hexene-1-ol and Pentostam in experimentally infected mice with Leishmania major

| Treatment Group | Post-Treatment Observations | |
|---|---|---|
| n = 15/group | Day 0 | Day 14 |
| Controls (infected) | Large lesions | Lesions breaking Palate involvement 4 dead |
| Pentostam (IP) | Large lesions | Large lesions breaking Palate involvement 1 dead |
| Geraniol trioxolane (IP) | Large lesions | Lesions breaking Palate involvement 4 dead |

TABLE 7-continued

Efficacy of Geraniol trioxolane, the trioxolane derivative of cis 3-hexene-1-ol and Pentostam in experimentally infected mice with Leishmania major

| Treatment Group n = 15/group | Post-Treatment Observations | |
|---|---|---|
| | Day 0 | Day 14 |
| Geraniol trioxolane (topical) | Large lesions | Dry lesions No palate involvement No death Healthy |
| Trioxolane derivative of cis 3-hexene-1-ol (IP) | Large lesions | Lesions scabbed 2 palate involvement 2 dead |
| Trioxoiane derivative of cis 3-hexene-1-ol (topical) | Large lesions | Lesions small and dry Animals healthy and active No death |

3.4 Treatment of mice infected with *Leishmania donova*

Balb/c mice were experimentally infected with *Leishmania donova*, the causative agent of visceral leishmaniasis. The infection was visceralized in 3–4 weeks. Infected mice were divided into four groups of 15 mice each. One group was treated with Geraniol trioxolane, another with the trioxolane derivative of cis 3-hexene-1-ol and the third group with Pentostam. The fourth group was kept as a control group. Each medication was used at 20 mg/kg body weight and given in 0.5 ml intraperitoneal, daily doses for 5 days. The average weights of mice were 20 g each.

Mice were examined after the 5 days of treatment and every week thereafter. Indicators of response to treatment were examination of visceral organs for the parasites in autopsied mice, plus the general well-being of the living.

Preliminary results of this study indicate that both Geraniol trioxolane and the trioxolane derivative of cis 3-hexene-1-ol perform better than Pentostam in clearing parasites from the viscera, such as the spleen.

4. CLINICAL STUDIES IN HUMANS 4.1 Clinical Studies on Candidiasis

We have begun clinical studies to assess the efficacy of Geraniol trioxolane and the trioxolane derivative of cis 3-hexene-1-ol in the treatment of common infections, including those that are considered as common opportunistic infections in HIV-infected persons. The patients recruited in the present studies are those who volunteered themselves to participate in the studies.

Candidiasis is a particular opportunistic infection which is common in HIV infected individuals. Vaginal candidiasis is a very common infection suffered by virtually all women at one time or another. Thus, we have performed clinical studies on this fungal infection as follows:

4.1.1 25 ml of a liquid preparation containing 25 mg/ml of the product was applied three times a day in the oropharyngeal area in ten patients with oral candidiasis. The infection cleared within 5 days and did not require additional treatment.

4.1.2 Vaginal inserts were formulated and used twice a day in five female volunteers suffering from vaginal candidiasis, and a further three having both vaginal candidiasis and gram positive cocci infections. As in oral candidiasis, these infections cleared within 5 days and required no further treatment.

4.2 Clinical Studies on Systemic Infections 4.2.1 AIDS: A minimum of 10 patients have been followed over a period of from 2 to 4 years on a dosage regimen of approximately 200 milligrams daily. All patients have shown improvement and stabilization of both clinical and laboratory parameters of disease.

4.2.2 CANCER: 4 patients have been treated over a period of from 2 to 4 years. These include one Adenocarcinoma of the Lung, one Hodgkins Disease, and two Lymphomas. Patients were treated on a daily dose basis of 200 milligrams daily. In all patients, during the course of treatment, there was regression of tumor or cessation of growth of tumor, as well as improvement in clinical parameters. One patient demonstrated reinstitution of tumor growth with forced cessation of therapy. The other patients remain in remission.

4.2.3 RHEUMATOID ARTHRITIS: 4 patients with long-standing active RA were placed on a dose of 200 milligrams daily. All patients had evidence of remission of symptoms within 2 weeks, and in all patients all evidence of active disease had cleared within 6–8 weeks. Patients have remained asymptomatic with no evidence of progression of disease for two years.

4.2.4 OSTEOARTHRITIS AND INFLAMMATORY POLYARTHRITIS: 10 patients, including those with degenerative, psoriatic and arthritis associated with chronic fatigue syndrome, as well as non-specific polyarthritis were studied. These patients were treated with a daily dose of 200 milligrams. All patients showed substantial or complete disappearance of all symptoms within 8 weeks. All patients have been maintained without symptom and without evidence of progression of disease.

4.2.5 CHRONIC FATIGUE SYNDROME: 4 patients were treated with 200 milligrams daily. All patients showed marked improvement. All symptoms were completely or substantially cleared within 3 months.

4.2.6 LUPUS ERYTHEMATOSUS: 1 patient with associated colitis and arthritis. All signs and symptoms of active disease cleared within 90 days with complete resolution of arthritis, colitis and reduction of ANA titer from 1:1880 down to 1:30.

4.3 Clinical Studies on Topical Diseases 4.3.1 FUNGAL, DISEASES OF SKIN: 30 patients were treated for various forms of skin fungus unresponsive to other forms of therapy. All patients had complete clearing of skin lesions within 4–6 weeks. The lesions were treated with a 3% solution of active ingredient in propylene glycol once or twice daily, 4.3.2 BACTERIAL DISEASES OF SKIN:
i) ACNE: In a series of 40 patients with chronic acne vulgaris of varying degrees of severity, a 3% solution was applied to the lesions on a daily basis. All patients shows significant or marked clearing of lesions. New lesions formed less often and cleared quickly with subsequent applications.
ii) IMPETIGO: 3 patients had complete clearing within 1 week with application of 3% solution twice daily,
iii) PARONYCHIA: 4 patients. Lesions cleared rapidly and completely in all cases within 48 hours of beginning application of 3% solution.
iv) WOUND HEALING and SCAR PREVENTION: Various surgical and non-surgical wounds were treated with a 3% solution on a daily basis. Wounds so treated were shown to heal faster, with no evidence of secondary infection and noticeable reduction in scar formation. Those persons prone to keloid formation had no evidence of keloid formation with the use of this treatment.

4.3.3 VIRAL DISEASES OF THE SKIN:

i) HERPES: 40 patients comprising herpes simplex, genitalis, zoster, ophthalmic were treated with a topical solution of 3% active ingredient in propylene glycol, and in the case of ophthalmic with a fresh ½% solution in saline with a small amount of propylene glycol as solubilizing agent. In all herpes genitalis and simplex cases, all lesions when treated early showed rapid cessation of viral expression and rapid clearing of lesions in most cases, without evidence of blister formation. Most lesions cleared completely within 48 hours. Lesions which had progressed to significant size prior to treatment required 3-4 days for complete resolution. Herpes zoster (5 cases), all cases showed slow progressive resolution of lesions, with complete clearing in approximately 2-6 weeks. Most lesions had been present for up over 6 months. Ophthalmic herpes (2 cases), in both cases lesions showed definite early clearing, with resolution in one case within 48 hours and the other case in 4 days.

ii) VENEREAL WARTS: 4 patients. A solution of 3% active ingredient in was applied 3 times daily with complete clearing of all lesions in 2-3 weeks.
COMMON WARTS (MULTIPLE MANIFESTATIONS): 26 patients. 10% solution was applied 2 times daily. All patients shows resolution with treatment; however, there was marked variation in time to complete clearing, depending apparently upon the type of presentation of the wart. Some warts cleared within 2 weeks, while most required several months and a few manifestations took over 1 year for complete clearing.

4.3.4 DERMATOLOGICAL:

i) ECZEMA: 14 patients. Various forms of exczema or neurodermatitis were treated and approximately ⅓ showed complete resolution of lesions within 6 weeks. Approximately 30% showed significant improvement and the remainder showed only slight or no improvement.

ii) PSORIASIS: 13 patients. A group of patients with various degrees of severity were treated. Milder cases were treated with topical application of 3% solution, and there was marked or complete resolution of lesions in all but 2 cases. 3 cases of severe generalized dermatitis were treated with a combination of 3% topical once or twice daily, or with systemic dosage of 200 milligrams 3 times weekly. All showed complete clearing of lesions within 6-8 weeks.

iii) INSECT BITES: Multiple cases of insect bites, including those of mosquito, bee, wasp, fly, flea, totalling in excess of 20 patients were treated. All lesions showed almost immediate relief of pain, itching, with rapid reduction of swelling and erythema. All lesions cleared completely within 24 to 48 hours.

iv) CORAL BURNS/JELLYFISH STINGS: 18 patients. All pain, swelling and erythema was alleviated rapidly with either complete clearing or minor residual erythema within 24 hours.

v) POISON OAK: 3 patients. Application of 3% solution provided marked and immediate relief of itching, and in 2 cases with complete clearing of lesions within 48 hours.

vi) SEBORRHEIC DERMATITIS: 10 patients. Lesions involving the scalp and eyebrows were treated with once daily applications with marked response and reduction of lesions in 9 out of the 10 cases.

vii) BURNS: 19 patients with first and second degree burns. Most patients reported immediate and substantial or complete relief of pain. Most patients showed evidence of the development of buliae and there was rapid and substantial reduction in swelling and erythema in all patients. No third degree burns were treated.

4.4 Clinical Studies on Arthritis 4.4.1 ARTHRITIS: 5 patients of relatively severe arthritis of small joints were treated with 6% topical applications twice daily. All patients reported marked or complete relief of pain within 2 weeks.

4.5 Clinical Studies on Dental and Oral Conditions:

4.5.1 PHARYNGITIS: 17 patients with varying degrees of tonsillitis or pharyngitis were treated with topical application of 3% active ingredient in glycerin 4 times each day. All patients showed moderate to rapid relief of pain with reduction of swelling in the first 24 hours. Complete resolution was seen in all patients within 48 to 72 hours.

4.5.2 TOOTH ACHE: 7 patients with varying degrees of dental pain from tooth ache experienced immediate and substantial relief from pain with application of 3% topical solution to the surrounding gums.

4.5.3 GINGIVITIS: 3 patients with gingivitis had a marked or complete resolution within 3 months upon using 3-4 drops 3% geraniol trioxolane in glycerine with toothpaste.

4.6 Clinical Studies on Oral Manifestations of Bacterial Overgrowth:

4.6.1 HALITOSIS: 10 patients with chronic halitosis all reported marked or complete resolution of the halitosis with daily use of four drops of 3% solution in glycerin during brushing of teeth.

4.6.2 CANKER SORES: 9 patients. All patients reported rapid resolution of pain and discomfort with complete clearing of lesions within 24 to 48 hours by application of 3% solution 3 times a day.

4.7 GYNECOLOGICAL:

4.7.1 SPERMICIDE: A pilot study using 4 couples using a vaginal suppository of 1.5% solution in high molecular weight polyethylene glycol (Plurocols) over a 4-month program and there has been no evidence of conception to date.

4.7.2 HEMORRHOIDS: 21 patients with hemorrhoids ranging from small external symptomatic hemorrhoids to large external and internal bleeding hemorrhoids. All cases showed substantial or complete resolution within 1 week using 3% topical solution or a combination of topical and rectal suppository.

5. CONCLUSION

From the data obtained so far, it is clear that the two products are effective against an extremely wide spectrum of bacteria, fungi, viruses and protozoa. They have also been observed to be spermicidal, as well as immunomodulatory. There is no recognized toxicity or undesirable side effect associated with their use. These products are therefore believed to be potent drugs for use in a very wide range of activities.

Both Geraniol trioxolane and the trioxolane derivative of cis 3-hexene-1-ol are potentially active compounds against a variety of organisms, notable ones being protozoa (Leishmania spp.), both gram positive and gram negative bacteria, and fungi. An additional activity observed in vitro is their ability to kill spermatozoa and cultured myeloma cells. On the basis of the results from ongoing studies on safety and toxicity, the products are believed safe for human use as drugs.

In addition to the clinical data obtained on Geraniol trioxolane and the trioxolane derivative of cis 3-hexene-1-ol, we have obtained clinical data using erucic acid ozonated in accordance with the method of Example 1. This ozonated compound is active in vitro against a wide variety of bacterial and fungal pathogens. The compound has successfully been used topically in a propylene glycol base at 2% active material to treat genital and oral herpes, fungal infections, wasp stings, eczema, and diaper rash. In addition, a three-month trialon three ARC (AIDS Related Complex) patients and one lymphoma patient, remission of disease was maintained after an initial treatment with geraniol trioxolane resulted in remission.

The trioxolane and diperoxide derivatives of both terpene and non-terpene unsaturated hydrocarbons are aH believed to have the same mechanism of action. While not wishing to be bound by any particular mode of action, it is believed that these compounds release pharmacologically active zwitterion moieties upon hydrolysis. In view of the compounds' perceived common mechanism of action, it is believed that a wide variety of diperoxide and trioxolane derivatives of terpene and non-terpene unsaturated hydrocarbons have activities similar to the activities reported in this section for Geraniol trioxolane and the trioxolane derivative of cis 3-hexene-1-ol.

I claim:

1. A pharmaceutical composition for the treatment of a medical condition in a mammal, comprising a pharmaceutically effective amount for treatment of said condition of a diperoxide derivative of a non-terpene unsaturated hydrocarbon in a pharmaceutically acceptable, non-aqueous carrier wherein said derivative is prepared by passing ozone through said hydrocarbon under conditions that provide for intimate contact between said hydrocarbon and said ozone at a temperature of 35° C. or below.

2. The pharmaceutical composition of claim 1 in the form of a toothpaste.

3. The pharmaceutical composition of claim 1 in the form of a mouthwash.

4. The pharmaceutical composition of claim 1 in the form of a rectal or vaginal suppository.

5. The pharmaceutical composition of claim 1 in the form of a topical preparation.

6. The pharmaceutical composition of claim 1 in a form suitable for sublingual application.

7. The pharmaceutical composition of claim 1 in a form suitable for parenteral administration.

8. The pharmaceutical composition of claim 7 applied to a condom.

9. The pharmaceutical composition of claim 1 in combination with soap.

10. The pharmaceutical composition of claim 1, wherein said hydrocarbon comprises a compound selected from the group consisting of 3-hexene-1-ol and erucic acid.

11. A pharmaceutical composition for the treatment of a medical condition in a mammal, comprising a pharmaceutically effective amount for treatment of said condition of a trioxolane derivative of a non-terpene unsaturated hydrocarbon in a pharmaceutically acceptable, non-aqueous carrier wherein said derivative is prepared by passing ozone through said hydrocarbon under conditions that provide for intimate contact between said hydrocarbon and said ozone at a temperature of below 20° C.

* * * * *